(12) United States Patent
Yamashita et al.

(10) Patent No.: US 7,968,901 B2
(45) Date of Patent: Jun. 28, 2011

(54) LIGHT EMITTING UNIT

(75) Inventors: Shinji Yamashita, Tachikawa (JP);
Masato Toda, Hachioji (JP)

(73) Assignee: Olympus Medical Systems Corp. (JP)

( * ) Notice: Subject to any disclaimer, the term of this patent is extended or adjusted under 35 U.S.C. 154(b) by 65 days.

(21) Appl. No.: 12/025,113

(22) Filed: Feb. 4, 2008

(65) Prior Publication Data

US 2008/0128740 A1    Jun. 5, 2008

Related U.S. Application Data

(63) Continuation of application No. PCT/JP2006/315320, filed on Aug. 2, 2006.

(30) Foreign Application Priority Data

Aug. 5, 2005    (JP) .................................. 2005-228332

(51) Int. Cl.
*H01L 33/00* (2010.01)
(52) U.S. Cl. .................... 257/99; 257/100; 257/E23.057
(58) Field of Classification Search .................... 257/99, 257/100, E23.057
See application file for complete search history.

(56) References Cited

U.S. PATENT DOCUMENTS

| | | | |
|---|---|---|---|
| 3,593,070 A | 7/1971 | Reed | |
| 6,943,380 B2 * | 9/2005 | Ota et al. | 257/100 |
| 7,473,934 B2 * | 1/2009 | Nagai et al. | 257/89 |
| 2001/0007051 A1 * | 7/2001 | Nakashima | 600/179 |
| 2004/0188696 A1 | 9/2004 | Hsing Chen et al. | |
| 2005/0006754 A1 | 1/2005 | Arik et al. | |
| 2006/0198162 A1 * | 9/2006 | Ishidu et al. | 362/623 |

FOREIGN PATENT DOCUMENTS

| | | |
|---|---|---|
| JP | 7-45868 | 2/1995 |
| JP | 10-178214 | 6/1998 |
| JP | 11-267099 | 10/1999 |
| JP | 11-318806 | 11/1999 |
| JP | 2000-150969 | 5/2000 |
| JP | 2003-24276 | 1/2003 |
| JP | 2004-165308 | 6/2004 |
| WO | WO 2005/032356 | 4/2005 |

OTHER PUBLICATIONS

International Search Report mailed Nov. 7, 2006 in PCT/JP2006/315320.
English translation of International Preliminary Report dated Feb. 14, 2008 corresponding to International Application No. PCT /JP2006/315320.
Letter from German associate dated Nov. 27, 2009 forwarding the Search Report dated Nov. 17, 2009 to Japanese associate, including discussion of relevancy thereof.
Search Report issued by European Patent Office in connection with corresponding application No. EP 06 78 2189 on Nov. 17, 2009.

* cited by examiner

*Primary Examiner* — Tan N Tran
(74) *Attorney, Agent, or Firm* — Ostrolenk Faber LLP (57) ABSTRACT

A light emitting unit includes at least one electrode member having high thermal conductivity and low resistance, and one or more flip-chip-type light emitting device of which an anode electrode side or a cathode electrode side is connected to the electrode member, and wherein the electrode member extends in a longitudinal direction thereof, and heat generated in the light emitting device is to be released along the longitudinal direction of the electrode member.

3 Claims, 11 Drawing Sheets

LIGHT EMITTING UNIT

CROSS REFERENCE TO RELATED APPLICATIONS

This is a Continuation Application of PCT Application No. PCT/JP2006/315320, filed Aug. 2, 2006, which was published under PCT Article 21(2) in Japanese.

This application is based upon and claims the benefit of priority from prior Japanese Patent Application No. 2005-228332, filed Aug. 5, 2005, the entire contents of which are incorporated herein by reference.

BACKGROUND OF THE INVENTION

1. Field of the Invention

The present invention relates to a light emitting unit on which a light emitting device such as an LED is mounted.

2. Description of the Related Art

Heretofore, it has been suggested that an LED as a light emitting device should be incorporated in an endoscope. For example, it is suggested that the LED should be arranged in an operating section of the endoscope and illuminative light from the LED should be guided to an endoscope distal end portion by a light guide to irradiate, whereby the subject is illuminated. In such a system, however, a light quantity is largely lost while the illuminative light passes through the light guide, and hence the sufficient light quantity cannot be obtained.

To obtain the sufficient light quantity, it can be contrived that an LED package is incorporated in the endoscope distal end portion. However, in the LED package of the large light quantity, a current of several hundred milliamperes or more needs to flow through the LED in order to obtain the large light quantity, and a comparatively large amount of heat is generated in the LED. In the large light quantity LED package, a heat release mechanism for releasing the thus generated heat is required, and hence a diameter of the package increases. Therefore, when the conventional large light quantity LED package is used in the endoscope distal end portion, a diameter of the endoscope distal end portion increases.

Moreover, the conventional large light quantity LED package has a configuration wherein the package is mounted in a face-up manner and subjected to wire bonding, or a configuration wherein the package is mounted on a silicon substrate or a sub-mount device in a face-down manner to connect electrodes from the sub-mount substrate to a lead frame via the wire bonding. In such a configuration, however, the heat generated in the LED cannot be efficiently released. Therefore, in the case where the conventional large light quantity LED package is used in the endoscope distal end portion, there become problems that the light quantity decreases, noise of an image pickup device increases, and the endoscope distal end portion becomes hot, through the heat generation.

An endoscope disclosed in Jpn. Pat. Appln. KOKAI Publication No. 2003-24276 includes at least one light emitting device as an illuminative light source, and a printed wiring board on which this light emitting device is mounted and which is arranged at a distal end of an insertion portion of the endoscope. In the surface of the printed wiring board, a ground conductor pattern is formed by an area excluding areas occupied by signal conductor patterns except a ground conductor pattern and insulating areas.

BRIEF SUMMARY OF THE INVENTION

In a aspect of the present invention, a light emitting unit includes: at least one electrode member having high thermal conductivity and low resistance; and one or more flip-chip-type light emitting device of which an anode electrode side or a cathode electrode side is connected to the electrode member, and wherein the electrode member extends in a longitudinal direction thereof, and heat generated in the light emitting device is to be released along the longitudinal direction of the electrode member.

In an aspect of the present invention, a light emitting assembly includes: at least two light emitting units, wherein the light emitting unit includes: at least one electrode member having high thermal conductivity and low resistance; and one or more flip-chip-type light emitting device of which an anode electrode side or a cathode electrode side is connected to the electrode member, and the electrode member extends in a longitudinal direction thereof, and heat generated in the light emitting device is to be released along the longitudinal direction of the electrode member, and the electrode members of at least the two light emitting units extend in a common longitudinal direction; and a common electrode member having high thermal conductivity and low resistance, and thermally and electrically connected to the anode side or cathode side electrode member of each of at least the two light emitting units.

In an aspect of the present invention, an endoscope includes the light emitting unit including: at least one electrode member having high thermal conductivity and low resistance; and one or more flip-chip-type light emitting device of which an anode electrode side or a cathode electrode side is connected to the electrode member, and wherein the electrode member extends in a longitudinal direction thereof, and heat generated in the light emitting device is to be released along the longitudinal direction of the electrode member.

In an aspect of the present invention, a medical device includes the light emitting unit including: at least one electrode member having high thermal conductivity and low resistance; and one or more flip-chip-type light emitting device of which an anode electrode side or a cathode electrode side is connected to the electrode member, and wherein the electrode member extends in a longitudinal direction thereof, and heat generated in the light emitting device is to be released along the longitudinal direction of the electrode member.

In an aspect of the present invention, an endoscope includes the light emitting assembly including: at least two light emitting units, wherein the light emitting unit includes: at least one electrode member having high thermal conductivity and low resistance; and one or more flip-chip-type light emitting device of which an anode electrode side or a cathode electrode side is connected to the electrode member, and the electrode member extends in a longitudinal direction thereof, and heat generated in the light emitting device is to be released along the longitudinal direction of the electrode member, and the electrode members of at least the two light emitting units extend in a common longitudinal direction; and a common electrode member having high thermal conductivity and low resistance, and thermally and electrically connected to the anode side or cathode side electrode member of each of at least the two light emitting units.

BRIEF DESCRIPTION OF THE SEVERAL VIEWS OF THE DRAWING

The accompanying drawings, which are incorporated in and constitute a part of the specification, illustrate embodiments of the invention, and together with the general descrip

DETAILED DESCRIPTION OF THE INVENTION

A first embodiment of the present invention will hereinafter be described with reference to FIGS. 1 to 6.

Figure 1:
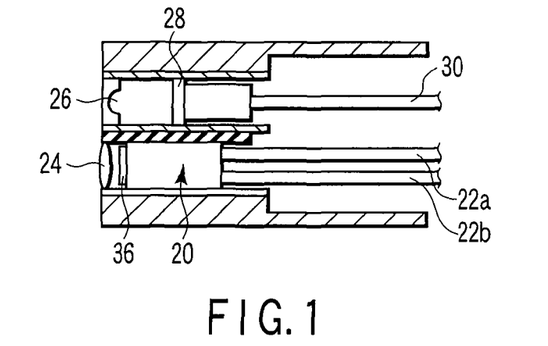
- FIG. 1 is a longitudinal sectional view showing an endoscope distal end portion according to a first embodiment of the present invention.

Referring to FIG. 1, an endoscope according to the present embodiment is a forward-viewing type endoscope, and a light emitting unit 20 on which an LED chip 36 is mounted as a light emitting device is arranged at a distal end portion of an insertion portion of the endoscope. This light emitting unit 20 is connected to LED driving cables 22a, 22b to transmit various signals for driving the LED chip 36. Illuminative light generated by the light emitting unit 20 is emitted to a subject via an illumination lens 24. Reflected light from the subject is focused by an objective lens 26 on a CCD 28 and picked up.

The CCD 28 is connected to a CCD cable 30 to transmit various signals for driving the CCD 28 and an image signal get through the picking up of the CCD 28.

A method of mounting the LED chip according to the first embodiment of the present invention will be described with reference to FIGS. 2A to 2C.

Figure 2A:
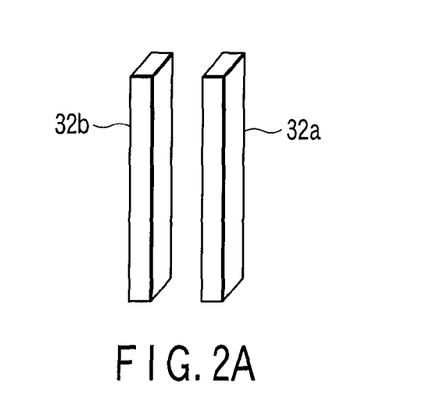
FIG. 2A is an explanatory view of a first step of a method of mounting an LED chip according to the first embodiment of the present invention.
Figure 2B:
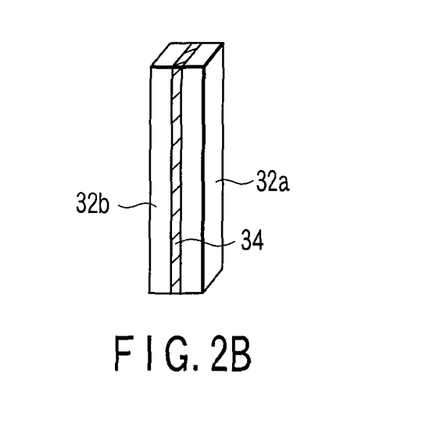
FIG. 2B is an explanatory view of a second step of the method of mounting the LED chip according to the first embodiment of the present invention.
Figure 2C:
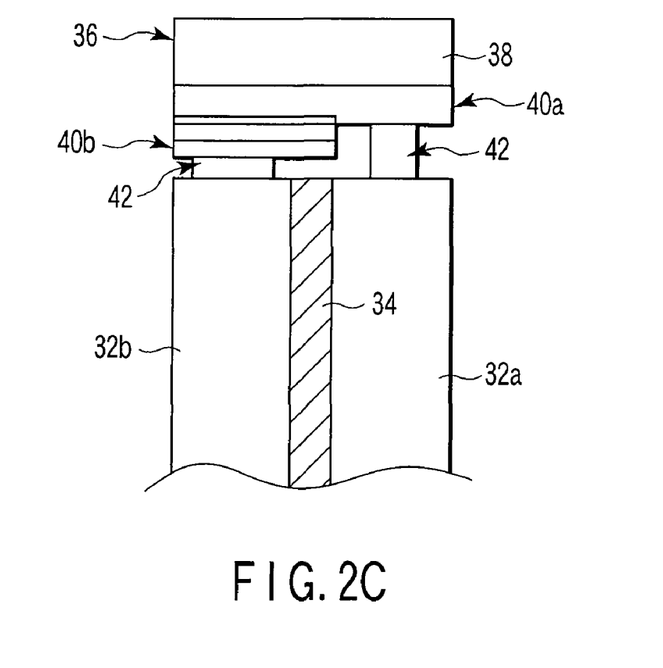
FIG. 2C is an explanatory view of a third step of the method of mounting the LED chip according to the first embodiment of the present invention.

Referring to FIG. 2A, in a first step, a pair of substantially rod-shaped electrode members 32a, 32b having high thermal conductivity and low resistance are prepared. The electrode members 32a, 32b are made of a composite material of, for example, Cu and Al or C and Cu. Referring to FIG. 2B, in a second step, the pair of electrode members 32a, 32b are integrated via an insulating layer 34. The pair of electrode members 32a, 32b and the insulating layer 34 extend in a common longitudinal direction. Referring to FIG. 2C, in a third step, the LED chip 36 is prepared. This LED chip 36 is a flip-chip-type LED chip, a cathode electrode 40a is laminated on a sapphire substrate 38, and an anode electrode 40b is laminated on an area of a part of the cathode electrode 40a. Then, the LED chip 36 is directly bonded to the electrode members 32a, 32b in a face-down state. In more detail, the anode electrode 40b and the cathode electrode 40a of the LED chip 36 are directly bonded to distal end surfaces of the electrode members 32b, 32b, respectively, with a resin or the like (see reference number 42 in FIG. 2C).

Figure 3:
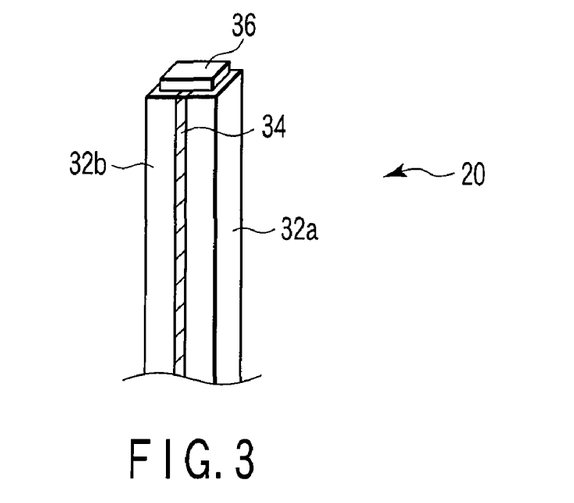
FIG. 3 is a perspective view showing a light emitting unit according to the first embodiment of the present invention.

Referring to FIGS. 1 and 3, in this manner, the LED chip 36 is arranged at the distal end surfaces of the pair of substantially rod-shaped electrode members 32a, 32b. Here, the common longitudinal direction of the pair of electrode members 32a, 32b and the insulating layer 34 substantially matches with a longitudinal direction of the insertion portion of the endoscope. The electrode members 32a, 32b directly come in contact with an inner surface of an endoscope distal end member forming the distal end of the insertion portion of the endoscope, and thermally connected to the inner surface.

Figure 4:
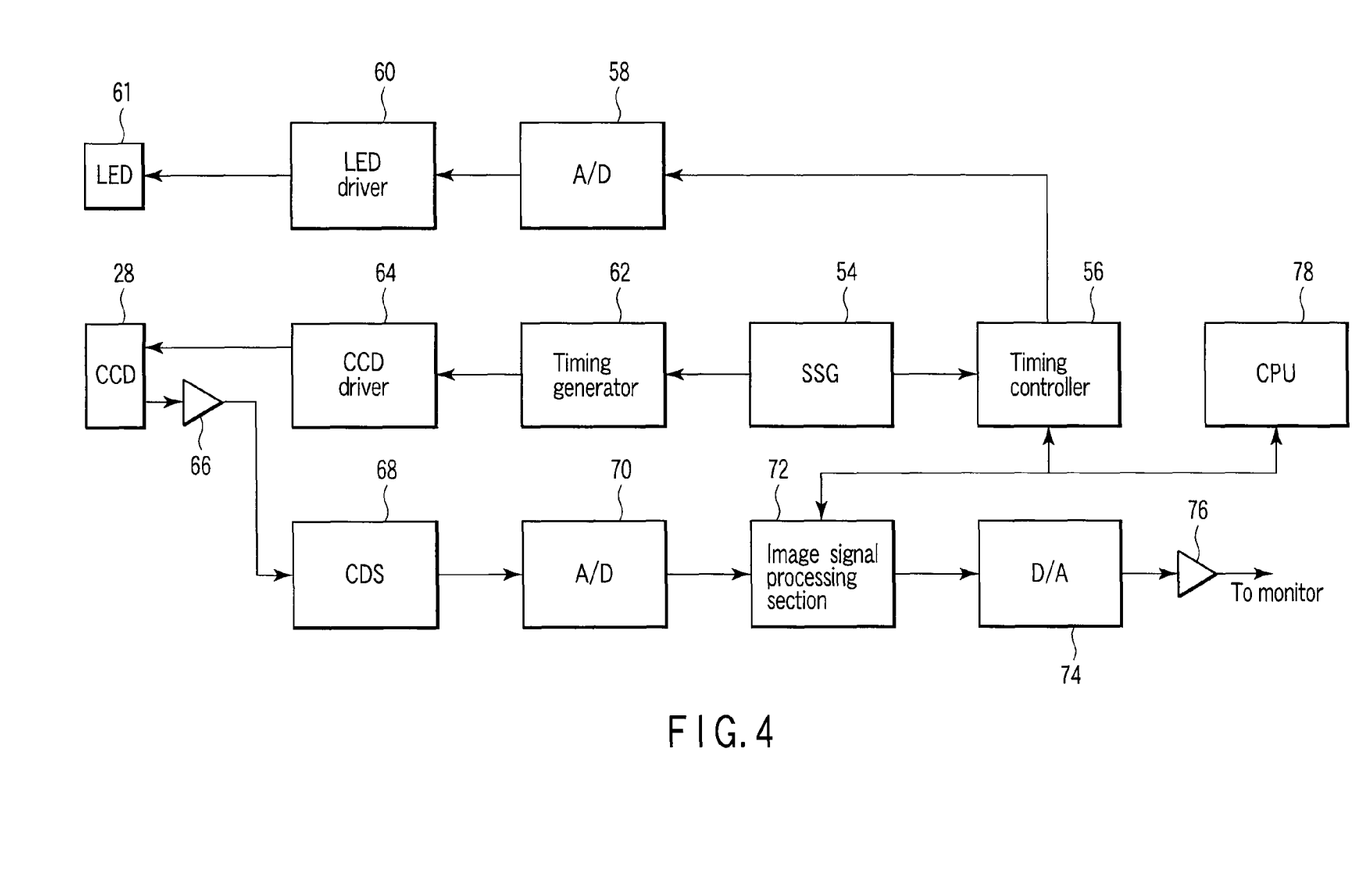
FIG. 4 is a block diagram of an endoscope according to the first embodiment of the present invention.

An electric configuration for illumination and observation in the endoscope will be described with reference to FIG. 4.

A control signal is generated by a timing controller 56 based on a vertical sync signal (VD) generated by a sync signal generator (SSG) 54. The control signal from the timing controller 56 is converted into a digital signal by an analog-to-digital converter 58. An LED driver 60 generates a driving signal for driving an LED 61 based on this control signal. The LED 61 emits light in response to this driving signal. In the present embodiment, the LEDs 61 of colors R, G and B are used.

On the other hand, based on the vertical sync signal (VD) generated by the SSG 54, a timing generator 62 generates a control signal. A CCD driver 64 generates a driving signal for driving the CCD 28 based on the control signal from the timing generator 62. An image signal acquired by the CCD 28 is amplified by an amplifier 66, and noise components are removed by a correlation double sampling (CDS) circuit 68. Afterward, the image signal is converted into a digital signal by an analog-to-digital converter 70, input into an image signal processing section 72 and subjected to processing such as white balance, interpolation processing, contour emphasis or γ-processing. The image signal is converted into an analog signal by a digital-to-analog converter 74, amplified by an amplifier 76 and displayed in a monitor. A CPU 78 is a portion which controls an operation of sections including the image signal processing section 72 and the timing controller 56.

Figure 5:
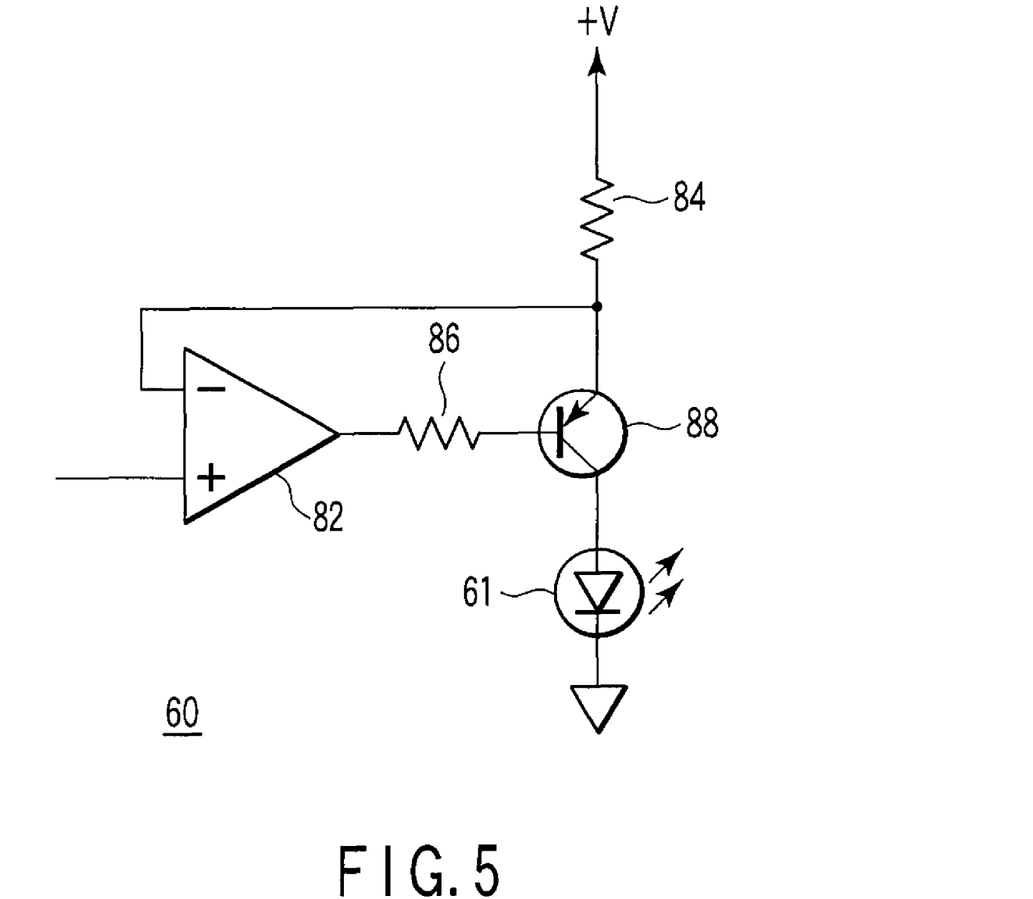
FIG. 5 is a block diagram showing an LED driver according to the first embodiment of the present invention.

The LED driver 60 will be described in detail with reference to FIG. 5. The LED 61 driven through power supply is connected to an operation amplifier 82, resistances 84, 86 and a transistor 88 in order to control driving and a light quantity of the LED.

Figure 6:
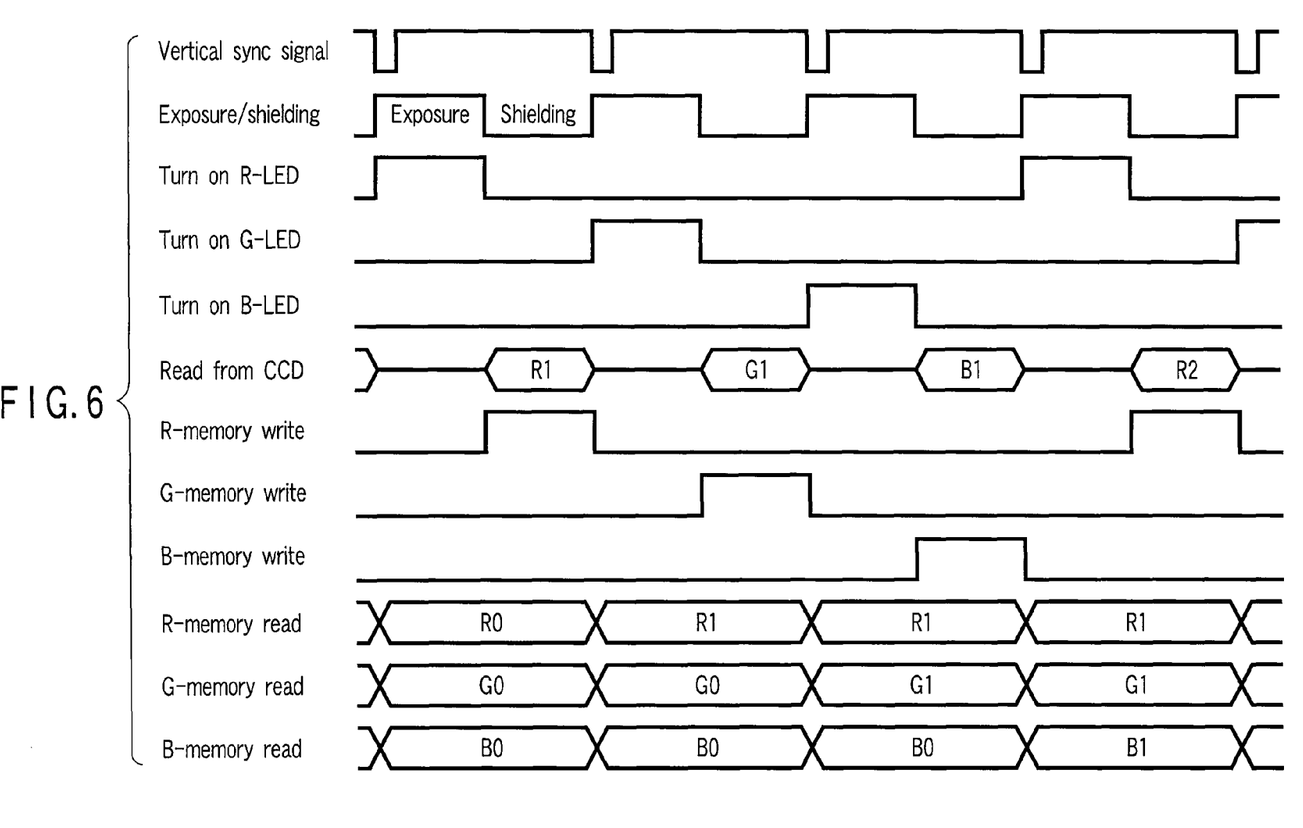
FIG. 6 is a timing chart showing a flow of signal processing in the endoscope according to the first embodiment of the present invention.

The signal processing in the endoscope will be described with reference to FIG. 6.

In an exposure period, the LED 61 is lit, the reflected light from the subject enters the CCD 28, and charges are generated by photoelectric conversion and stored in the CCD 28. In a shielding period, the LED 61 is turned off, the light is intercepted so that the light does not enter the CCD 28, and the charges accumulated in the CCD 28 are read. More specifically, the LEDs 61 of the colors R, G and B are successively lit based on the vertical sync signal (VD) generated by the SSG 54. Then, the charges picked up and accumulated in the CCD 28 in the exposure period are successively read for each of the colors R, G and B in the shielding period, and written in memories of R, G and B, respectively. Then, in reading, data is read in order of R, G and B. Reading of G data is started while the R data is read, and B data is read while the G data is read, so that a data reading time is reduced. The reflected light from the subject is taken into and picked up in the CCD 28 in this manner.

Therefore, the endoscope of the present embodiment produces the following effect.

According to the present embodiment, the heat can be released in the longitudinal direction via the electrode members, and hence a space in a lateral direction for the heat release may be small at the endoscope distal end portion. In consequence, a diameter of the endoscope distal end portion can be reduced, and layout for arrangement of devices at the endoscope distal end portion is facilitated.

Moreover, since the heat release in the longitudinal direction in accordance with a configuration of the endoscope is facilitate, heat release efficiency of the LED itself improves, and drop of the light quantity of the LED due to confinement of the heat can be prevented. Since an ambient temperature of the CCD 28 arranged at the endoscope distal end portion drops, generation of heat noise is inhibited, and further a sufficient light quantity can be secured while suppressing a temperature rise at the endoscope distal end portion.

Furthermore, since a bonding wire and a substrate can be omitted, an area viewed from an illuminating direction can be reduced. That is, the endoscope distal end portion can be miniaturized, and the diameter thereof can be reduced. In addition, cost reduction can be achieved through the omitting of step.

Figure 7:
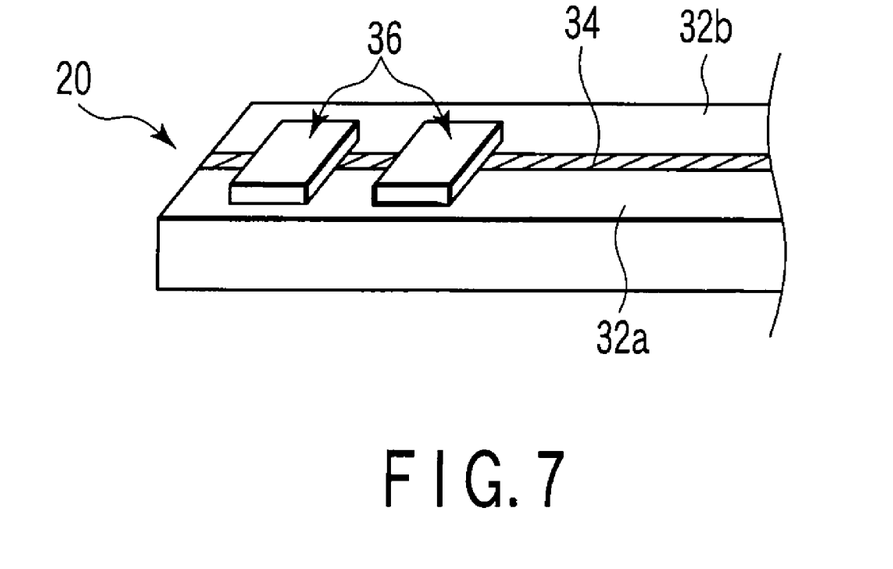
FIG. 7 is a perspective view showing a light emitting unit according to a second embodiment of the present invention.

FIG. 7 shows a second embodiment of the present invention. A component having a function similar to that of the first embodiment is denoted with the same reference numbers, and description thereof is omitted. The endoscope of the present embodiment is a side-viewing type endoscope. In the light emitting unit 20, the LED chips 36 are arranged at side surfaces of distal ends of the substantially rod-shaped electrode members 32a, 32b.

Figure 8:
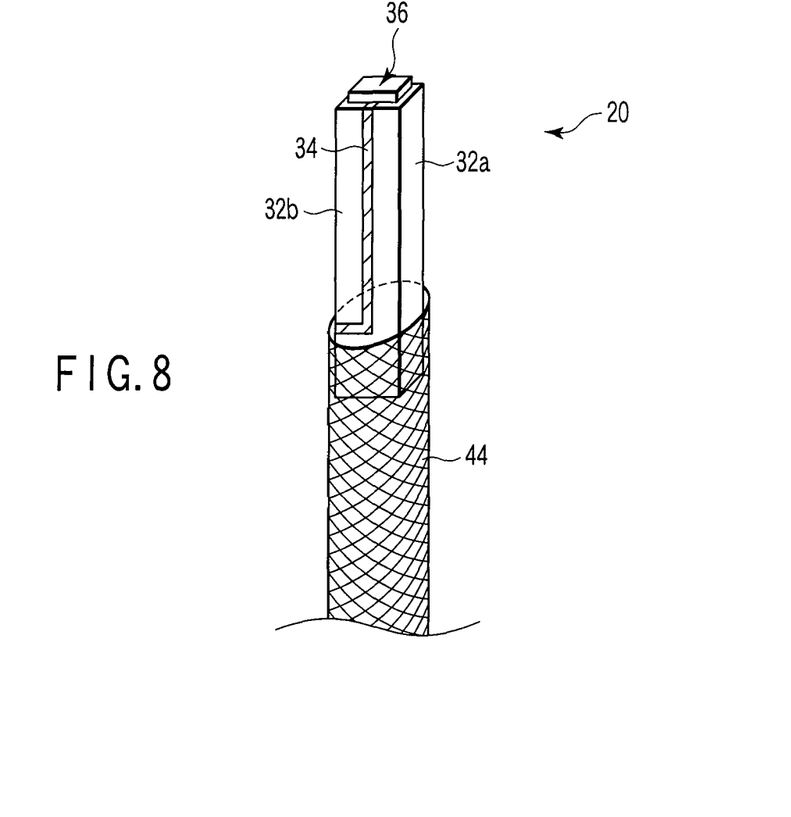
FIG. 8 is a perspective view showing a light emitting unit according to a third embodiment of the present invention.

FIG. 8 shows a third embodiment of the present invention. A component having a function similar to that of the first embodiment is denoted with the same reference numbers, and description thereof is omitted. In the light emitting unit 20 of the present embodiment, the one electrode member 32a has an L-shape. Then, a distal end of a mesh-like heat sink member 44 are fixed and thermally connected to proximal ends of the electrode members 32a, 32b. Heat from the LED chip 36 is released via the electrode members 32a, 32b and further this heat sink member 44.

Figure 9A:
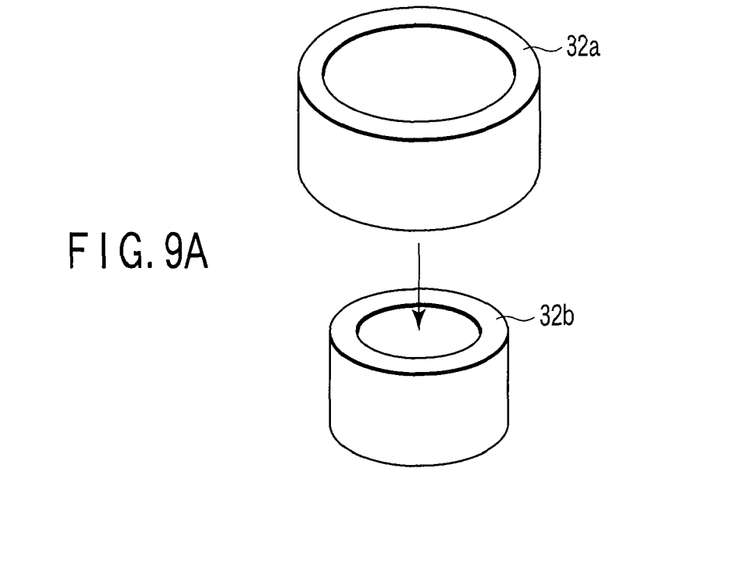
FIG. 9A is an explanatory view of a first step of a method of mounting an LED chip according to a fourth embodiment of the present invention.
Figure 9B:
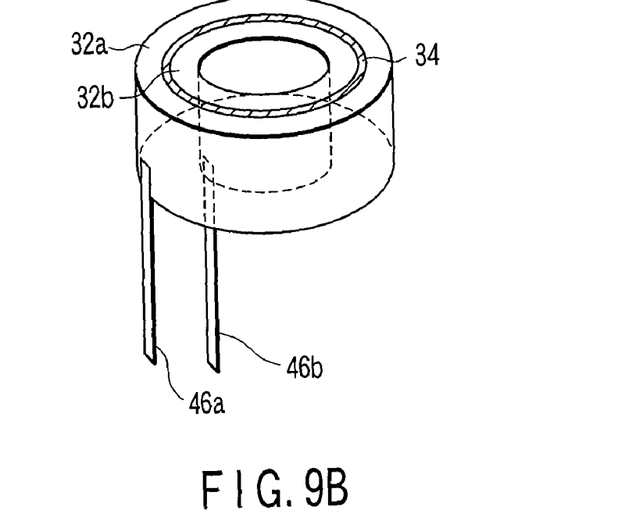
FIG. 9B is an explanatory view of a second step of the method of mounting the LED chip according to the fourth embodiment of the present invention.
Figure 9C:
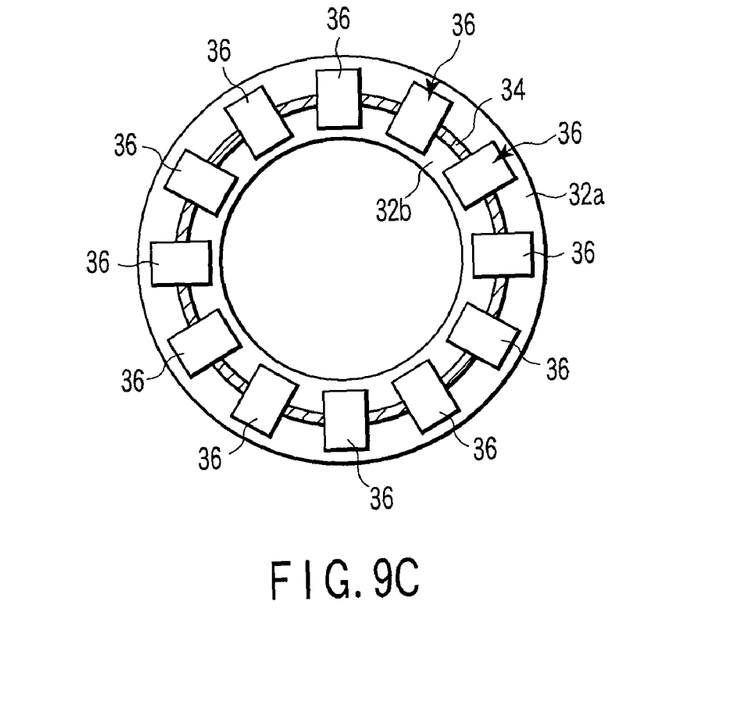
FIG. 9C is an explanatory view of a third step of the method of mounting the LED chip according to the fourth embodiment of the present invention.

FIGS. 9A to 9C show a fourth embodiment of the present invention. A component having a function similar to that of the first embodiment is denoted with the same reference numbers, and description thereof is omitted.

The method of mounting the LED chip according to the present embodiment will be described with reference to FIGS. 9A to 9C.

Referring to FIG. 9A, in a first step, the pair of electrode members 32a, 32b substantially ring-shaped and having high conductivity and low resistance are prepared. In the pair of electrode members 32a, 32b, an inner diameter of one electrode member 32a is larger than an outer diameter of the other electrode member 32b. Referring to FIG. 9B, in a second step, the pair of electrode members 32a, 32b are integrated via an insulating layer 34. Here, the pair of electrode members 32a, 32b and the insulating layer 34 are concentrically arranged, and an axial direction of a central axis of them is a common longitudinal direction. Then, lead wires 46a, 46b are connected to the pair of electrode members 32a, 32b, respectively. Referring to FIG. 9C, in a third step, the anode electrode sides of a plurality of the LED chips 36 is directly bonded to an end surface of one electrode member 32b, and the cathode electrode sides thereof is directly bonded to an end surface of the other electrode member 32a. Preferably, the anode electrode side is connected to the inner electrode member 32b, and the cathode electrode side is connected to the outer electrode member 32a, so that the cathode electrode side which generates more heat can be cooled more.

Figure 10:
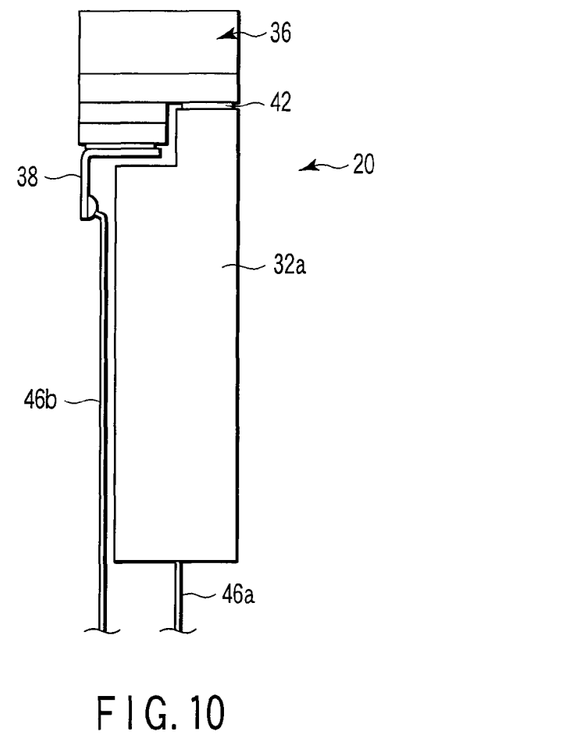
FIG. 10 is a side view showing a light emitting unit according to a fifth embodiment of the present invention.

FIG. 10 shows a fifth embodiment of the present invention. A component having a function similar to that of the first embodiment is denoted with the same reference numbers, and description thereof is omitted.

In the present embodiment, the single electrode member 32a is used. That is, the single electrode member 32a substantially rod-shaped and having high thermal conductivity and low resistance is directly bonded to the cathode electrode side (or the anode electrode side) of the one or more flip-chip-type LED chip 36 via a resin or the like. Furthermore, the anode electrode side (or the cathode electrode side) of the LED chip 36 is connected to the lead wire 46b via the substrate 38, and heat is released via the lead wire 46b.

Figure 11:
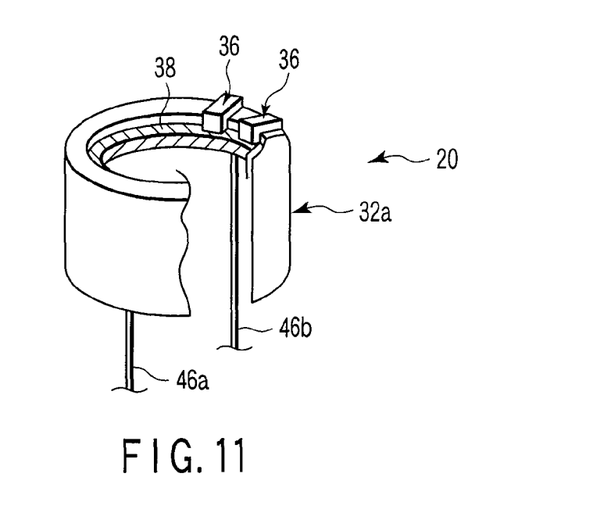
FIG. 11 is a perspective view showing a light emitting unit according to a sixth embodiment of the present invention.

FIG. 11 shows a sixth embodiment of the present invention. A component having a function similar to that of the first embodiment is denoted with the same reference numbers, and description thereof is omitted.

In the present embodiment, the single electrode member 32a substantially ring-shaped and having high thermal conductivity and low resistance is directly bonded to the cathode electrode side (or the anode electrode side) of the one or more flip-chip-type LED chip 36 via a resin or the like.

Figure 12:
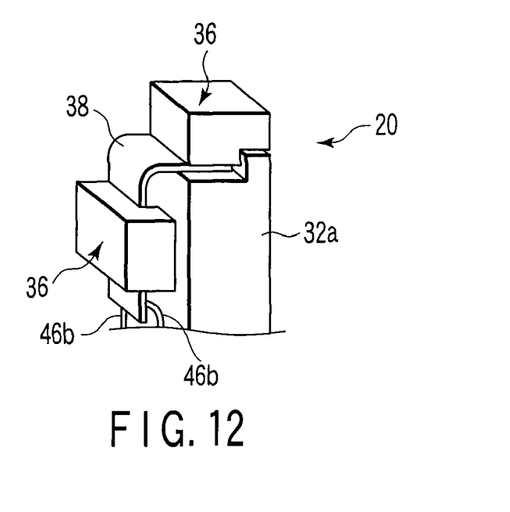
FIG. 12 is a perspective view showing a light emitting unit according to a seventh embodiment of the present invention.

FIG. 12 shows a seventh embodiment of the present invention. A component having a function similar to that of the first embodiment is denoted with the same reference numbers, and description thereof is omitted.

The endoscope of the present embodiment is an endoscope configured to switch the forward-viewing and the side-viewing. Then, in the light emitting unit 20, the LED chips 36 are arranged at the distal end surface and the distal end side surface of the electrode member 32a substantially rod-shaped and having high thermal conductivity and low resistance. Here, the cathode electrode connected to the cathode electrode side of the LED chips 36 is commonly used in the two LED chips 36, but the anode electrodes connected to the anode electrode side are independently provided in the substrate 38.

In the fifth to seventh embodiments, the only cathode electrode side of the LED chip 36 having a large amount of heat generation is directly bonded to the electrode member 32a, whereby heat conduction in the cathode electrode is promoted, and a heat release property improves. The cathode electrode is thermally connected to an exterior metal of the endoscope distal end member or the like, so that the heat release of the whole endoscope distal end can be achieved. Furthermore, since a process of integrating the pair of electrode members via the insulating layer is not required, costs can be reduced by the process.

Figure 13:
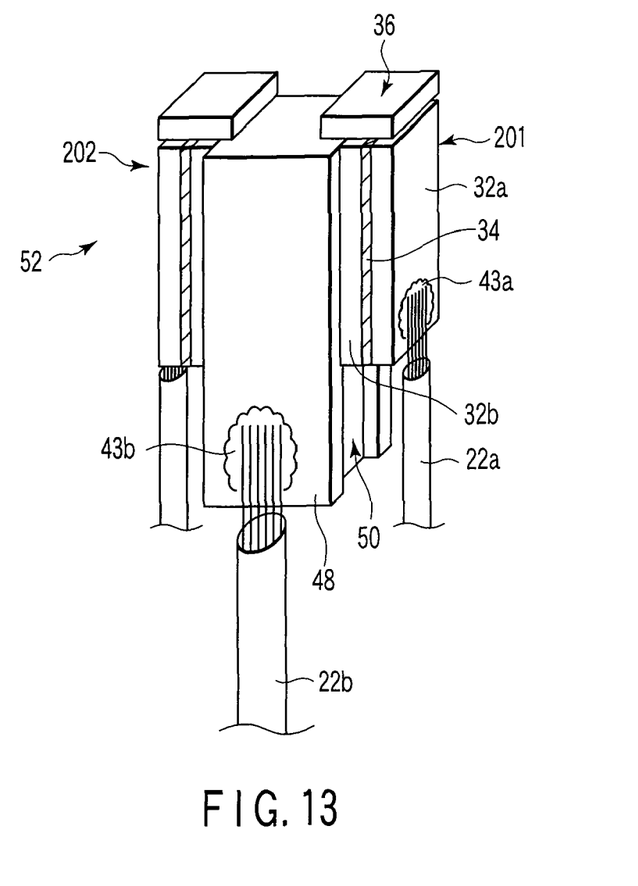
FIG. 13 is a perspective view showing a light emitting assembly according to an eighth embodiment of the present invention.
Figure 14:
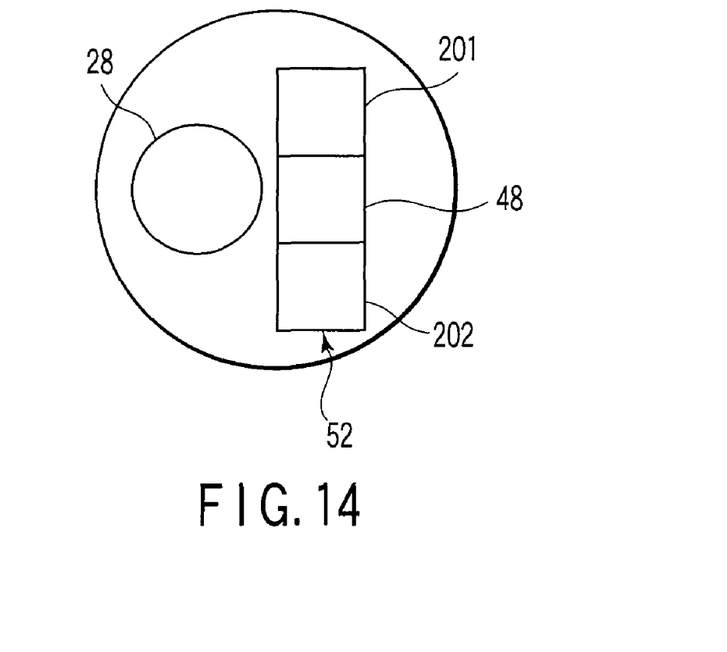
FIG. 14 is a transverse sectional view showing the light emitting assembly according to the eighth embodiment of the present invention.

FIGS. 13 and 14 show a seventh embodiment of the present invention. A component having a function similar to that of the first embodiment is denoted with the same reference numbers, and description thereof is omitted.

Referring to FIGS. 13 and 14, in the present embodiment, first and second light emitting units 201, 202 having a configuration similar to the light emitting unit of the first embodiment are used. A distal end of the cathode side LED driving cable 22a is soldered to the cathode side electrode member 32a of the first light emitting unit 201 (see 43a in the drawing). This also applies to the second light emitting unit 202. Moreover, the anode side electrode member 32b of the first light emitting unit 201 and the anode side electrode member 32b of the second light emitting unit 202 are bonded to a pair of opposite side surfaces of a common electrode member 48 substantially rectangular parallelepiped block-shaped and having high thermal conductivity and low resistance. The electrode members 32a, 32b of the first and second light emitting units 201, 202 and the common electrode member 48 extend in the common longitudinal direction. This common longitudinal direction substantially matches with the longitudinal direction of the insertion portion of the endoscope. In the present embodiment, the electrode members 32b of the first and second light emitting units 201, 202 are fitted to groove portions 50 extended in the common electrode member 48, respectively. Therefore, a contact area between the electrode member 32b and the common electrode member 48 increases, and heat conduction from the electrode member 32b to the common electrode member 48 is promoted. Then, a distal end of the anode side LED driving cable 22b is soldered to the common electrode member 48 (see 43b in the drawing). A light emitting assembly 52 is formed in this manner.

It is to be noted that the distal end of the mesh-like heat sink member may be fixed and thermally connected to a proximal end of the common electrode member 48, and the heat sink member may further release heat.

Figure 15:
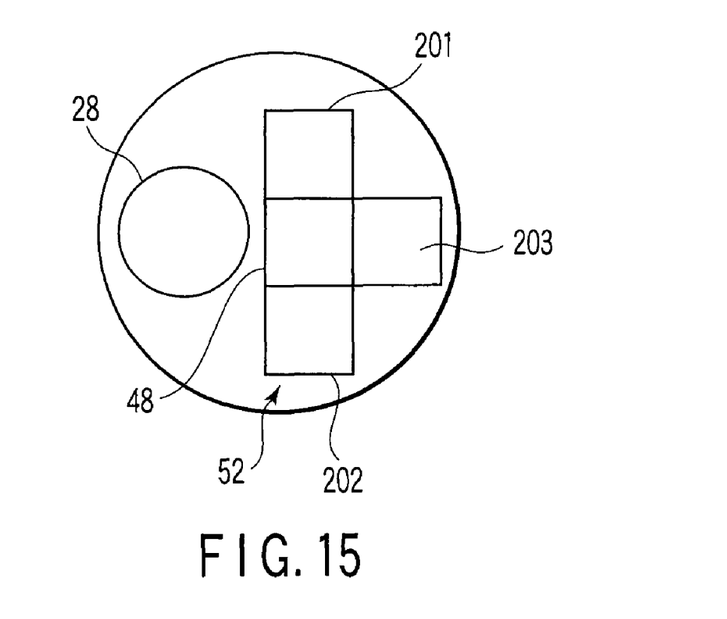
FIG. 15 is a transverse sectional view showing another light emitting assembly according to the eighth embodiment of the present invention.

Referring to FIG. 15, a third light emitting unit 203 may be further bonded to one side surface of the common electrode member 48, so that three light emitting units 201, 202 and 203 and the common electrode member 48 may form the light emitting assembly. Even in this case, the first to third light emitting units 201, 202 and 203 and the common electrode member 48 extend in the common longitudinal direction.

Therefore, the endoscope of the present embodiment produces the following effect.

In the endoscope of the present embodiment, in addition to the electrode members 32a of the light emitting units 201, 202 and 203, the common electrode member 48 releases the heat, and a heat release property is improved. Since the common electrode member 48 is used for the plurality of light emitting units 201, 202 and 203, the light emitting assembly is miniaturized, the endoscope distal end portion can be miniaturized and the diameter of the endoscope distal end portion can be reduced, or layout at the endoscope distal end portion is facilitated.

Moreover, the light emitting units 201, 202 and 203 having the same configuration can be used as a plurality of light emitting units 201, 202 and 203, and the light emitting units 201, 202 and 203 can be formed as a module. Therefore, an optimum light emitting assembly for the layout at the endoscope distal end portion and a required illumination characteristic and the like can be inexpensively and easily formed.

Furthermore, according to the light emitting assembly of the present embodiment, the anode side LED driving cable 22a can be used in common, and assembling with the endoscope distal end portion is facilitated as compared with a case where the separate LED driving cables are used. Since the light emitting assembly integrated beforehand may be assembled with the endoscope distal end portion, the assembling is facilitated as compared with a case where the plurality of light emitting units 201, 202 and 203 are individually assembled. In this manner, an assembling property is improved.

In addition, according to the light emitting assembly of the present embodiment, the cathode side LED driving cables 22b are independent from each other, and the respective light emitting units 201, 202 and 203 can independently be controlled. Therefore, when the subject is illuminated, the light quantity is adjusted for each of the light emitting units 201, 202 and 203, so that an appropriate light distribution property can be realized in accordance with a shape of the subject or the like. Although each LEDs has a slightly different light emitting characteristic with respect to a current even through the LEDs have the common standard, fluctuations of the light quantity for each LED can be corrected to obtain uniformly illuminative light through the independent control of the currents to the light emitting units 201, 202 and 203.

It is to be noted that in the light emitting assembly of the present embodiment, the anode side electrode members 32b of the plurality of light emitting units 201, 202 and 203 are bonded to the common electrode member 48, but the cathode side electrode members 32a may be bonded to the common electrode member 48. In this case, the cathode side LED driving cable 22a may be constituted in common.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A light emitting unit comprising:
   a pair of electrode members having high thermal conductivity and low resistance, being substantially rod-shaped and including end surfaces, respectively;
   an insulating layer integrally interposed only between the pair of electrode members; and
   a flip-chip-type light emitting device connected to the pair of electrode members in a face-down state and including an anode electrode directly bonded to the end surface of the one electrode member and a cathode electrode directly bonded to the end surface of the other electrode member, and
   wherein the pair of electrode members and the insulating layer extend in a common longitudinal direction thereof,
   the light emitting unit is configured to be incorporated in an endoscope insertion portion, and a common longitudinal direction of the lair of electrode members and of the insulating layer is configured to substantially match a longitudinal direction of the endoscope insertion portion; and
   heat generated in the light emitting device is to be released along the common longitudinal direction of the pair of electrode members and the insulating layer.

2. An endoscope comprising a light emitting unit including:
- a pair of electrode members having high thermal conductivity and low resistance, being substantially rod-shaped and including end surfaces, respectively;
- an insulating layer integrally interposed only between the pair of electrode members; and
- a flip-chip-type light emitting device connected to the pair of electrode members in a face-down state and including an anode electrode directly bonded to the end surface of the one electrode member and a cathode electrode directly bonded to the end surface of the other electrode member, and
- wherein the pair of electrode members and the insulating layer extend in a common longitudinal direction thereof, the light emitting unit is incorporated in an endoscope insertion portion, and a common longitudinal direction of the pair of electrode members and of the insulating layer substantially matches a longitudinal direction of the endoscope insertion portion, and
- heat generated in the light emitting device is to be released along the common longitudinal direction of the pair of electrode members and the insulating layer.

3. The endoscope according to claim 2, wherein the light emitting unit is incorporated in an endoscope distal end portion, and thermally connected to an endoscope distal end member.

* * * * *